(12) United States Patent
Ishida et al.

(10) Patent No.: US 8,021,371 B2
(45) Date of Patent: Sep. 20, 2011

(54) MEDICAL WIRE

(75) Inventors: Jiro Ishida, Setsu (JP); Hironori Takata, Setsu (JP); Atsushi Ogawa, Kanagawa (JP)

(73) Assignees: Kaneka Corporation, Osaka-Shi (JP); Kaneka Medix Corporation, Osaka-Shi (JP)

( * ) Notice: Subject to any disclaimer, the term of this patent is extended or adjusted under 35 U.S.C. 154(b) by 1165 days.

(21) Appl. No.: 11/577,086

(22) PCT Filed: Oct. 27, 2005

(86) PCT No.: PCT/JP2005/019800
§ 371 (c)(1),
(2), (4) Date: Apr. 11, 2007

(87) PCT Pub. No.: WO2006/046651
PCT Pub. Date: May 4, 2006

(65) Prior Publication Data
US 2009/0227899 A1    Sep. 10, 2009

(30) Foreign Application Priority Data
Oct. 29, 2004   (JP) ................................ 2004-315131

(51) Int. Cl.
 *A61F 11/00*    (2006.01)
(52) U.S. Cl. ...................................... 606/108; 623/1.11
(58) Field of Classification Search .................. 606/108, 606/198, 200, 1, 194, 41; 623/1.11; 337/168, 337/169, 171; 607/97, 98, 113
See application file for complete search history.

(56) References Cited

U.S. PATENT DOCUMENTS

| | | | | |
|---|---|---|---|---|
| 5,458,596 A | * | 10/1995 | Lax et al. | 606/31 |
| 5,770,994 A | * | 6/1998 | Evans | 337/295 |
| 5,785,706 A | * | 7/1998 | Bednarek | 606/41 |
| 5,846,210 A | * | 12/1998 | Ogawa et al. | 600/585 |
| 5,984,929 A | | 11/1999 | Bashiri et al. | |
| 7,410,487 B2 | * | 8/2008 | Whayne | 606/49 |
| 7,572,257 B2 | * | 8/2009 | Whayne et al. | 606/49 |

FOREIGN PATENT DOCUMENTS

| | | |
|---|---|---|
| JP | 10-94542 | 4/1998 |
| JP | 2000-229086 | 8/2000 |
| JP | 2001-513390 | 9/2001 |

OTHER PUBLICATIONS

International Preliminary Report on Patentability and Written Opinion of the International Searching Authority dated May 10, 2007 (5 pages), issued in counterpart International Application No. PCT/JP2005/019800.

* cited by examiner

*Primary Examiner* — Gary Jackson
*Assistant Examiner* — Christopher Schubert
(74) *Attorney, Agent, or Firm* — Holtz, Holtz, Goodman & Chick, PC

(57) ABSTRACT

Disclosed herein is a medical wire with an intracorporeally indwelling member connected to the leading end part of a conductive wire body through a thermally-fusible connecting member, wherein expected heat generation can be achieved even when a conductive member that causes leak comes into contact with the leading end part of the conductive wire body, and thus the intracorporeally indwelling member can be surely released.
This medical wire comprises a conductive wire body and an intracorporeally indwelling member connected to the leading end part of the conductive wire body through a thermally-fusible connecting member, in which the connecting member is heated and fused by supplying an electric current for fusion through the conductive wire body, thereby releasing the intracorporeally indwelling member, wherein a non-conductive coating film is formed on an external peripheral surface of an electrode-forming portion in the leading end part of the wire body, and a part of the surface of the wire body is exposed through the coating film, thereby forming a heating electrode portion.

11 Claims, 4 Drawing Sheets

MEDICAL WIRE

CROSS-REFERENCE TO THE RELATED APPLICATIONS

This application is a national phase of the international application No. PCT/JP2005/019800 filed Oct. 27, 2005, the entire contents of which are incorporated by reference. This application also claims benefit of priority under 35 U.S.C. §119 to Japanese Application No. 2004-315131 filed Oct. 29, 2004, the entire contents of which are incorporated by reference.

TECHNICAL FIELD

The present invention relates to a medical wire used to leave an intracorporeally indwelling member at an intended site in a vital body.

BACKGROUND ART

Various problems are generally presented in treatment involving surgical operation to a vital body. For example, a patient undergoing an operation must withstand a long-time operation, has a relatively high danger of infection and often causes invasion. A surgeon, as well, is forced to endure intense concentration for the long period of operation.

In order to permit lightening such various stress and performing a necessary operation more safely and easily, catheters, guide wires and embolizing materials for occluding blood vessels and the like, and other various medical instruments have been developed in recent years and been put to practical use. With the recent advancement of medical instruments such as catheters and guide wires, an intravascular operation in which the intended affected part is approached through a blood vessel comes to be performed and often applied to treatments for diseases such as arteriovenous malformation, cerebral aneurysm and carotid-cavernous fistula.

As a method for treating aneurysm or the like, which causes little invasion, there is currently known vascular embolization in which an intracorporeally indwelling member composed of a metal, which does not exert an adverse influence on a vital body, such as platinum is left within aneurysm. In this method, a medical wire with the intracorporeally indwelling member connected to the leading end part of a delivery wire is inserted into a catheter arranged in the vital body, the wire is operated under observation by a radiography to guide the intracorporeally indwelling member to a desired position within the vital body, whereby the intracorporeally indwelling member is caused to reach the intended site, and the intracorporeally indwelling member is released in this state.

As a method for releasing the intracorporeally indwelling member, there are known mechanical means and electrical means. For example, as an electrically releasing means, there is a means of supplying an electric current between a conductive wire and a counter electrode connected to the vital body from the outside to decompose and fuse a connecting member (see, for example, Patent Art. 1 and Patent Art. 2).

Patent Art. 2 discloses a medical wire for vascular embolization in which an intracorporeally indwelling member is connected to the leading end part of a conductive wire through a thermally-fusible rod-like connecting member composed of polyvinyl alcohol. According to this medical wire, a high-frequency electric current is applied between the conductive wire and the counter electrode, whereby the leading end part of the conductive wire functions as an electrode for heating to thermally fuse the connecting member in a moment, and the intracorporeally indwelling member is separated from the conductive wire, so that the medical wire is said to have merits that the time required for a surgical operation can be shortened and burdens imposed on a patient and a surgeon can be lightened.

Patent Art. 1: Japanese Patent Registration No. 3007022; and Patent Art. 2: Japanese Patent Registration No. 2880070.

In the medical wire formed by using such a connecting member composed of thermally-fusible polyvinyl alcohol as disclosed in Patent Art. 2, however, the high-frequency current flows through an electrolyte in the vital body when the current is applied between the conductive wire and the counter electrode connected to the vital body. At this time, the leading end part of the conductive wire functions as a heating electrode to fuse the connecting member.

When it is specifically described, this conventional medical wire is formed by a conductive wire body 50, a connecting member 52 and an intracorporeally indwelling member 54 as illustrated in FIG. 9. More specifically, the leading end part of the conductive wire body 50 is formed by a coil piece 56, and the coiled intracorporeally indwelling member 54 is connected to this coil piece 56 through the thermally-fusible connecting member 52. An insulating coating film 58 is formed on an external peripheral surface of a region of the wire body 50 other than the leading end part and the base end part thereof, and a heating electrode portion is formed by an exposed coil portion E of the coil piece 56, which is exposed without the coating film 58.

A high-frequency current is supplied from the base end part 60 of the wire body 50, whereby Joule heat is generated at the heating electrode portion by an electric resistance produced between the electrode portion and an electrolyte solution of a body fluid of a vital body contacting therewith, and a temperature around the heating electrode portion is raised by this Joule heat to fuse the thermally-fusible connecting member 52, thereby separating the intracorporeally indwelling member 54 from the wire body 50.

In order to fuse the connecting member in such a manner, it is necessary to raise the temperature of the heating electrode portion. In order to achieve this, it is necessary to convert electric energy by electric power from a high-frequency power source device to thermal energy (Joule heat) by a resistance in the electrolyte or the like around the heating electrode portion. The quantity of this Joule heat generated is determined by the degree of an electric resistance value around the heating electrode portion.

In an actual operation for leaving the intracorporeally indwelling member, the resistance value in the heating electrode portion is greatly affected by an ambient environment in which the heating electrode portion is located. For example, in the treatment for aneurysm, it is generally necessary to fill a plurality of intracorporeally indwelling members each composed of a metal such as platinum at a considerably high density into the aneurysm. Therefore, when an intracorporeally indwelling member is left in the latter half of the treatment, the circumference of the heating electrode portion of the wire body is in a state that a plurality of the intracorporeally indwelling members previously arranged has been present.

When such an intracorporeally indwelling member previously arranged is in a state that it has unexpectedly come into contact with the exposed heating electrode portion of the wire body, a part of the high-frequency current supplied to the heating electrode portion flows to the intracorporeally indwelling member contacting to cause leak, and after all, a state that the surface area of a member acting as an electrode has been increased is created. As a result, the resistance value in the electrode portion becomes lowered.

In the state that the resistance value has been lowered as described above, the quantity of Joule heat generated becomes decreased. As a result, the thermally-fusible connecting member is not completely fused, and thus the intracorporeally indwelling member remains unseparated.

More specifically, when the area of the electrode increases in the case where the electric power supplied is fixed, a heating area increases though the total quantity of Joule heat generated is the same, so that the rising breadth of the temperature decreases. Thus, the connecting member cannot reach a fusing temperature, and so the fusing of the connecting member cannot be completely performed. After all, the intracorporeally indwelling member cannot be released unless a current for fusion is supplied repeatedly. In such a case, a doctor who is a surgeon is required to conduct a confirming operation that the wire is pulled back while viewing an image through an X-ray equipment for radiography in order to confirm the fact that the intracorporeally indwelling member has been separated from the wire. When the intracorporeally indwelling member is not separated from the wire as a result of this confirming operation, however, it is necessary to store the intracorporeally indwelling member in the aneurysm by operating a delivery wire again, and moreover seeking an appropriate position where the intracorporeally indwelling member previously arranged comes into no contact with the electrode portion of the wire body. In the worst case, there is a possibility that the other intracorporeally indwelling member previously arranged in the same aneurysm may be moved or forced out of the aneurysm when the wire has been pulled back, so that burdens and risks imposed on the patient and the doctor become great.

DISCLOSURE OF THE INVENTION

The present invention has been made on the basis of the foregoing circumstances and has as its object the provision of a medical wire with an intracorporeally indwelling member connected to the leading end part of a conductive wire body through a thermally-fusible connecting member, wherein expected heat generation can be achieved without causing leak at a heating electrode portion of the wire body even when an intracorporeally indwelling member previously arranged or any other conductive member (hereinafter also referred to as "leaking member") that causes leak comes into physical contact with the leading end part of the conductive wire body, and thus the intracorporeally indwelling member can be surely released.

A medical wire according to the present invention comprises a conductive wire body and an intracorporeally indwelling member connected to the leading end part of the conductive wire body through a thermally-fusible connecting member, in which the connecting member is heated and fused by supplying an electric current for fusion through the conductive wire body, thereby releasing the intracorporeally indwelling member, wherein a non-conductive coating film is formed on an external peripheral surface of an electrode-forming portion in the leading end part of the wire body, and a part of the surface of the wire body is exposed through the coating film, thereby forming a heating electrode portion.

In the above-described medical wire, the heating electrode portion may preferably be formed by a plurality of fine cutout portions formed in the coating film. In this case, the total area of the plurality of the cutout portions may preferably be at least 0.01 mm$^2$, and the thickness of the coating film may preferably be 0.001 to 0.1 mm.

The cutout portions may be composed of circular or elliptical openings, or semicircular or semi-elliptical depressed cutouts formed from the leading edge of the coating film, and at least one of the cutout portions may be composed of a depressed cutout formed from the leading edge of the coating film. In particular, the cutout portions may preferably be composed of three semicircular depressed cutouts formed from the leading edge in the coating film and three circular openings formed in a region located on a side at hand from the area where the semicircular depressed cutouts are formed.

It may be preferable that the intracorporeally indwelling member be formed by a coil material composed of a metal filament, and the maximum width of the cutout portions formed in the coating film be smaller than the outer diameter of the coil material forming the intracorporeally indwelling member.

The intracorporeally indwelling member may preferably be that selected from platinum, tungsten, gold, tantalum, iridium and palladium, and alloys thereof.

A material of the coating film may preferably be that selected from polytetrafluoroethylene, fluorinated ethylene-propylene resins, polyalkylene fluoride, polyethylene, polyethylene terephthalate, polyamide and polyimide.

In the medical wire according to the present invention, the non-conductive coating film is formed on the external peripheral surface of the electrode-forming portion in the leading end part of the conductive wire body, and a part of the surface of the wire body is exposed through the coating film, whereby the heating electrode portions are formed. Accordingly, a high-frequency current is supplied through the wire body, whereby Joule heat is generated by an electric resistance produced by the fact that a body fluid (electrolyte solution) of a living body is contacting with the exposed surface portions of the wire body forming the heating electrode portion, thereby fusing the thermally-fusible connecting member to release the intracorporeally indwelling member.

In addition, since the non-conductive coating film is formed on the external peripheral surface of the heating electrode portion, electrical connection of a leaking member such as an intracorporeally indwelling member previously arranged to the wire body can be surely prevented even when a situation that the leaking member comes into physical contact with the leading end part of the wire body occurs upon introduction of another intracorporeally indwelling member through a catheter. As a result, a high-frequency current supplied to the wire body does not flow into the leaking member, so that fusion of the connecting member can be surely performed to surely separate the intracorporeally indwelling member.

DESCRIPTION OF CHARACTERS

Figure 1:
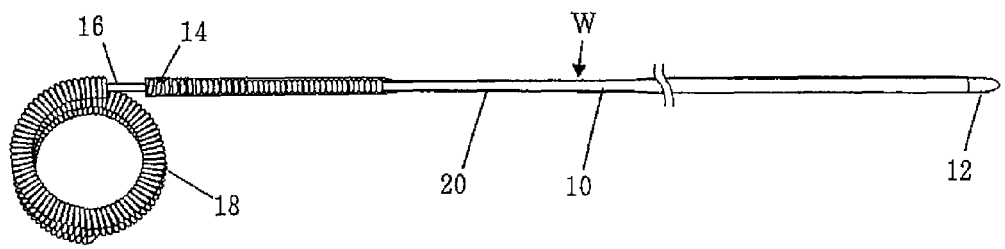
FIG. 1 is a side elevation illustrating the construction of an exemplary medical wire according to the present invention.

W Medical wire
10 Wire body
12 Base end part
14 Leading end part
16 Connecting member
18 Intracorporeally indwelling member
20 Coating film
22 Leading edge
24 Cutout portion
24A Opening
24B Depressed cutout
30 Container
31 Earth electrode
32 Physiological saline
33 Guiding catheter
34 Branched joint part
35 Microcatheter
36 High-frequency power source device
37 Output terminal
38 Leaking member
50 Wire body
52 Connecting member
54 Intracorporeally indwelling member
56 Coil piece
58 Insulating coating film
E Exposed coil portion
60 Base end part

BEST MODE FOR CARRYING OUT THE INVENTION

The present invention will hereinafter be described in detail with reference to the drawings.

FIG. 1 is a side elevation illustrating the construction of an exemplary medical wire according to the present invention, which has an intracorporeally indwelling member composed of a releasable or detachable embolizing coil. This medical wire W basically comprises a conductive wire body 10, a connecting member 16 and an intracorporeally indwelling member 18.

In the wire body 10, a leading end part 14 is formed by covering a portion on the leading end side of a tapered wire material made of a stainless alloy, the diameter of which gradually decreases from a base end part (right end side in the drawing) 12 thereof toward a leading end part, with a coil piece made of a stainless steel-platinum alloy and welding, and the outer diameter thereof is about 0.2 to 1.0 mm. An insulating coating film 20 is formed in a region, including the region of the leading end part 14, of the wire body 10, other than the base end part 12, in a state covering the external peripheral surface thereof.

A base end portion of the rod-like connecting member 16 is inserted into the coil piece of the leading end portion 14 of the wire body 10 and fixed, and a leading end portion of this connecting member 16 is inserted and fixed, thereby connecting and providing the coiled intracorporeally indwelling member 18.

The connecting member 16 serves to form a release portion for releasing the intracorporeally indwelling member 18 and is formed by a thermally-fusible material. As a specific material for the connecting member 16, may be preferably used that composed of a polyvinyl alcohol copolymer. In this case, the connecting member 16 can be fused by heating it to a temperature of, for example, at least 70° C. using high-frequency electric power. With respect to the dimensions thereof, for example, the outer diameter is about 0.05 to 0.50 mm, and the overall length is about 0.1 to 100 mm.

The intracorporeally indwelling member 18 illustrated is that obtained by further spirally winding a primary coil material obtained by spirally winding a filament made of a biocompatible material, for example, a platinum alloy, to form a secondary coil piece. The outer diameter of the filament that is a wire material is about 0.02 to 0.15 mm, the primary coil material has an outer diameter of about 0.1 to 1.2 mm and is flexible, and the outer diameter of the secondary coil piece is, for example, about 0.3 to 50 mm. However, the present invention is not limited thereto, and those having various dimensions are used according to an object of specific use and conditions. As the intracorporeally indwelling member, the primary coil material may be used as it is. The intracorporeally indwelling member may also be that formed by using the primary coil material and having another proper three-dimensional form than the secondary coil piece. The leading end of the primary coil material is preferably roundly machined into, for example, a semi-spherical form, thereby preventing the tissue of a vital body from being wounded when the coil piece is inserted.

As the material of the filament forming the intracorporeally indwelling member 18, may be used that selected from platinum, tungsten, gold, tantalum, iridium and palladium, and alloys thereof. Specifically, an alloy composed of platinum and tungsten is particularly preferred. The sectional form of the filament is not limited to a circular form, and those having various forms such as an elliptical form, square form and triangular form may also be used.

Figure 2:
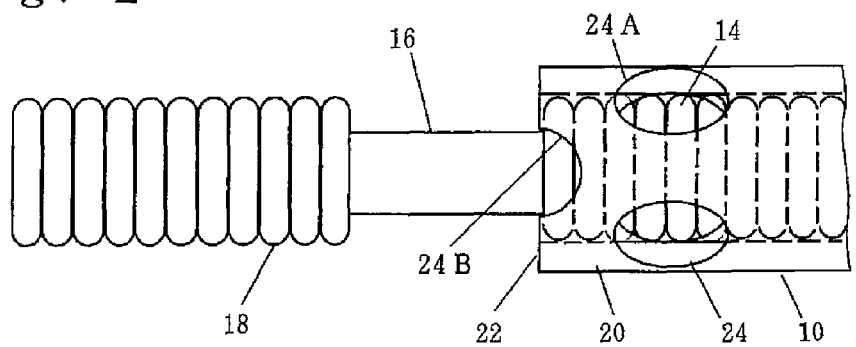
FIG. 2 is an explanatory side elevation illustrating, on an enlarged scale, a joint portion between a leading end part of a wire body and an intracorporeally indwelling member in the medical wire shown in FIG. 1.

FIG. 2 is an explanatory side elevation illustrating, on an enlarged scale, a joint portion between the leading end part 14 of the wire body 10 and the intracorporeally indwelling member 18. As illustrated in detail in this drawing, the coating film 20 is formed in a state covering the whole of a region including the coil piece forming the leading end part 14 of the wire body 10.

This coating film 20 can be formed by a non-conductive material, for example, that selected from various kinds of polymers having electrically insulating property, for example, polytetrafluoroethylene (PTFE), fluorinated ethylene-propylene resins (FEP), polyalkylene fluoride (PFA), polyethylene (PE), polyethylene terephthalate (PET), polyamide (PA) such as nylon, polyimide (PI), polyurethane, polypropylene, silicone resins and other resins. The thickness of this coating film 20 is preferably, for example, 0.001 to 0.1 mm, more preferably 0.01 to 0.1 mm.

In the coating film 20 formed in the region of the electrode-forming portion that is the leading end part 14 of the wire body 10, a plurality of fine cutout portions 24 are formed, and the cutout portions 24 make the external peripheral surface or external surface of the coil piece forming the leading end part 14 of the wire body 10 a state exposed. The heating electrode portion is formed by the exposed surface portions.

Figure 3:
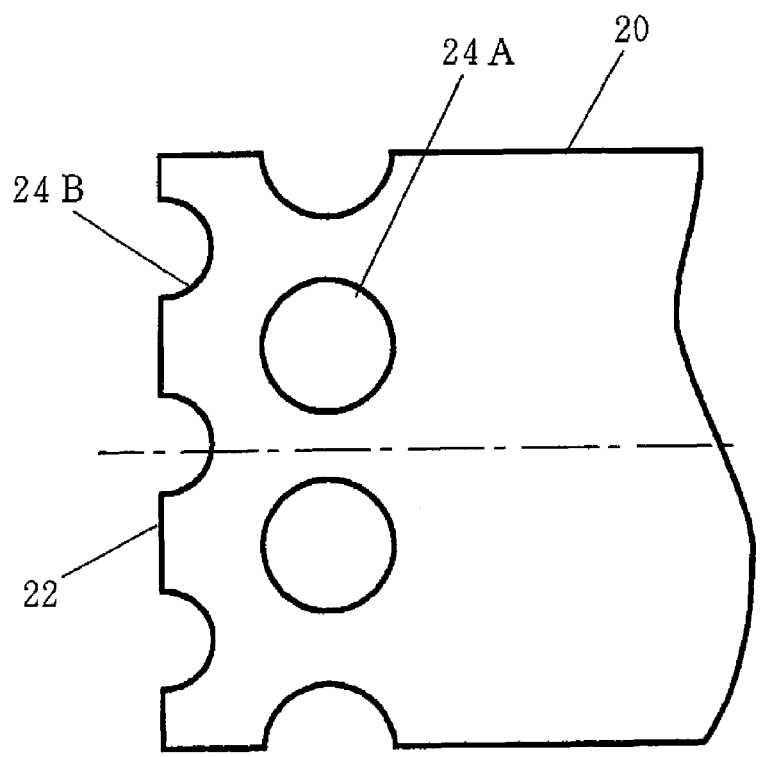
FIG. 3 is a development elevation illustrating a coating film, in which cutout portions have been formed, in an electrode-forming portion of the medical wire in the embodiment shown in FIG. 2.

Specifically, the cutout portions 24 in the embodiment shown in FIG. 2 are composed of three circular openings 24A formed through at positions close to a leading edge 22 of the coating film 20, which corresponds with the position of the leading end of the coil piece of the leading end part 14 of the wire body 10, and located in a row in a circumferential direction, and three semicircular depressed cutouts 24B formed from the leading edge 22 of the coating film 20 and located in a row in the circumferential direction as illustrated in FIG. 3.

Figure 4:
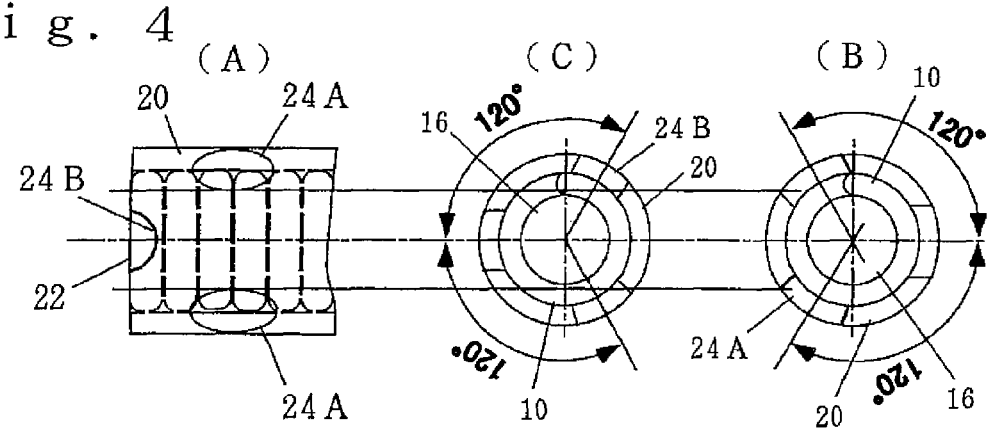
FIG. 4 is an explanatory view illustrating positions of openings and depressed cutouts making up the cutout portions in the embodiment shown in FIG. 2, in which (A) is a side elevation, (B) is a cross-sectional view illustrating the arrangement of the circular openings, and (C) is a cross-sectional view illustrating the arrangement of the semicircular depressed cutouts.

As illustrated in FIG. 4, each of the three circular openings 24A are located in a state different in an angle by 120° in the circumferential direction, and each of the three semicircular depressed cutouts 24B are also located in a state different in an angle by 120° in the circumferential direction. One circular opening 24A and a semicircular depressed cutout 24B adjoining this are located in a state different in an angle by 30° in the circumferential direction. Here, FIG. 4 is an explanatory view illustrating a positional relation of the openings and depressed cutouts making up the cutout portions in the above-described embodiment, in which (A) is a side elevation of the leading end part 14 of the wire body 10, (B) is a cross-sectional view illustrating the circumferential arrangement of the circular openings 24A, and (C) is a cross-sectional view illustrating the circumferential arrangement of the semicircular depressed cutouts 24B.

The cutout portions 24 are composed of one or both of the openings 24A by the through-holes formed in the coating film 20 and the depressed cutouts 24B formed at the leading edge portion of the coating film 20. When the opening 24A are circular, and when the depressed cutouts 24B are semicircular, the diameter thereof is, for example, 0.05 to 0.15 mm, and the number thereof is, for example, 1 to 20, whereby the total area of the cutout portions 24, i.e., the total area of the exposed surface portions in the leading end part 14 of the wire body 10 is preferably at least 0.01 mm².

Figure 5:
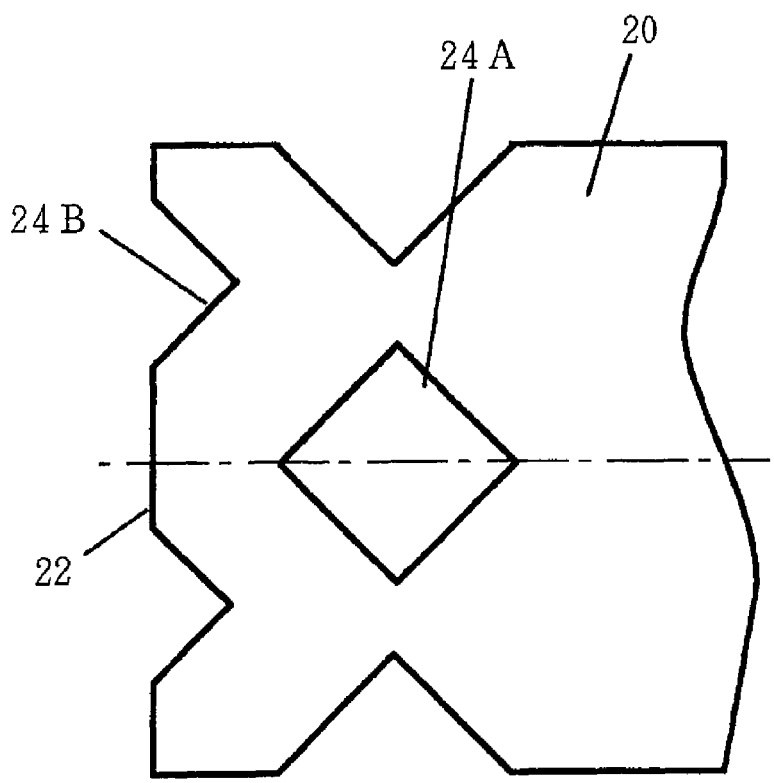
FIG. 5 is a development elevation illustrating a case where a cutout portion of another form has been formed in the coating film.

The form of the opening 24A making up each of the cutout portions 24 is not limited to the circular form, and any other proper form such as an elliptical, square or rectangular form may be adopted. However, it is preferable that the opening 24A be in the form of a circle, and the depressed cutout 24B be in the form of a semicircle, since a possibility that the coating film 20 may be broken due to the cutout portions 24 is small. FIG. 5 is a development elevation like FIG. 3, illustrating an embodiment of a coating film 20, in which square openings 24A and triangular depressed cutouts 24B have been formed.

Figure 6:
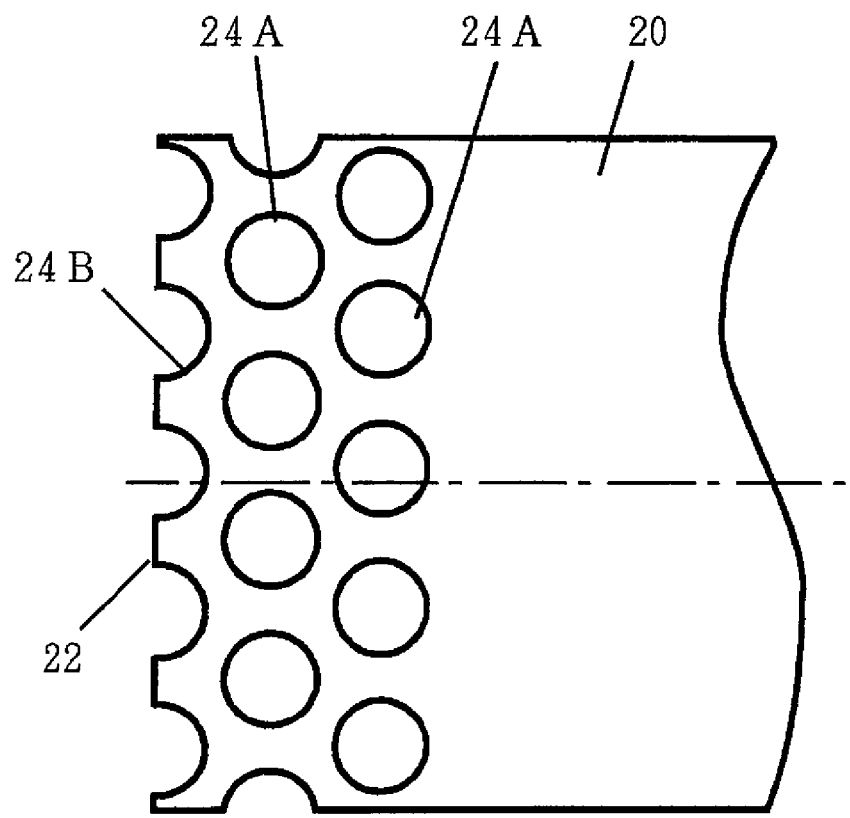
FIG. 6 is a development elevation illustrating a case where a cutout portion of another arrangement has been formed in the coating film.

No limitation is also imposed on the arrangements of the opening 24A and depressed cutouts 24B making up the cutout portions 24. For example, they may be arranged in various modes including an arrangement of radially several rows centering around an axis of the wire body 10. They may also be arranged without any order. FIG. 6 is a development elevation like FIG. 3, illustrating an embodiment of a coating film 20, in which circular openings 24A have been formed in two rows in a zigzag arrangement to each other together with semicircular depressed cutouts 24B.

As described above, the number of the opening and depressed cutouts making up the cutout portions 24, and the forms and arrangements thereof may be determined with a considerably great degree of freedom. It is however actually preferable that the maximum width of each of them, i.e., the maximum width in the exposed surface portions of the leading end part 14 be smaller than the outer diameter of the primary coil material forming the intracorporeally indwelling member. In this case, an effect that the direct contact of the intracorporeally indwelling member of the same construction, which has been previously arranged, i.e., the leaking member with the heating electrode portion composed of the exposed surface portions of the leading end part of the wire body is inhibited can be surely achieved even when the thickness of the coating film 20 is small.

EXAMPLES

Example 1

A stainless steel-made wire body 10 having a diameter of 0.23 mm and a length of 1800 mm was provided in accordance with the construction as shown in FIG. 1, and a coating film 20 composed of polytetrafluoroethylene (PTFE) and having a thickness of 0.02 to 0.04 mm was formed so as to cover an external peripheral surface of a region 1700 mm in length from a leading end part formed by a coil piece. Cutout portions 24 composed of circular openings 24A and semicircular depressed cutouts 24B, through which the external peripheral surface of the coil piece is exposed, were formed in the coating film 20 in a region continuing with the leading end in accordance with the embodiment shown in FIG. 3. The diameter of a circle relating to the openings 24A and depressed cutouts 24B is 0.06 mm, and a position of a line in a circumferential direction going through the centers of the three openings 24A is a position 0.8 mm away in a direction of a base end part from the leading edge of the coating film 20.

A base end portion of a columnar rod-like connecting member 16 composed of thermally-fusible polyvinyl alcohol and having a diameter of 0.1 mm and a length of 5 mm was inserted into the coil piece of the leading end part 14 of the wire body 10 formed in the above-described manner and bonded and fixed with an adhesive composed of cyanoacrylate. On the other hand, a primary coil material composed of a filament of a platinum alloy and having an outer diameter of 0.25 mm was wound in the form of a coil so as to give an outer diameter of 2 mm to form a secondary coil piece, thereby obtaining an intracorporeally indwelling member 18. A leading end portion of the connecting member 16 was inserted into the coil hole of the primary coil material of this intracorporeally indwelling member 18 and bonded and fixed with the adhesive composed of cyanoacrylate, thereby producing a medical wire.

Figure 7:
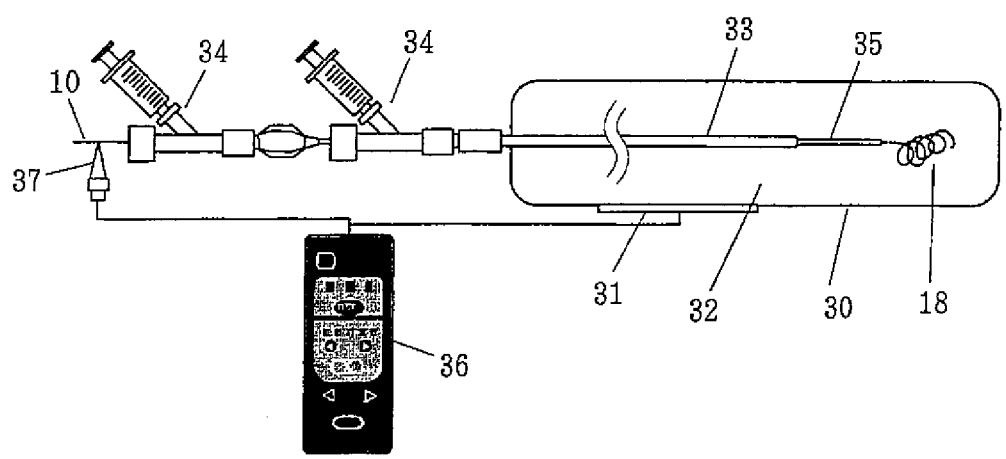
FIG. 7 typically illustrates a test for releasing an intracorporeally indwelling member in the medical wire of the construction shown in FIG. 1 to FIG. 3.

As illustrated in FIG. 7, an earth electrode 31 from a high-frequency power source device 36 was bonded to a stainless steel-made container 30, and physiological saline 32 was filled into container 30 and kept to a temperature of 37° C. On the other hand, a guiding catheter 33 having an inner diameter of 1.75 mm and a length of 600 mm was fixed to the container 30 in a state that the leading end thereof was immersed in the physiological saline 32. Further, a microcatheter 35 having an inner diameter of 0.4 mm and an overall length of 1500 mm was inserted from a branched joint part 34 provided at a proximal part of the guiding catheter 33 and fixed in a such a manner that the leading end thereof was immersed in the physiological saline 32.

In the apparatus of the above-described construction, the above-described medical wire was introduced with the intracorporeally indwelling member 18 in the lead from a proximal operating part of the microcatheter 35 located out of the container 30 and advanced until the connecting member 16 and the leading end part 14 of the wire body 10 reached a position of an opening of the microcatheter 35.

Figure 8:
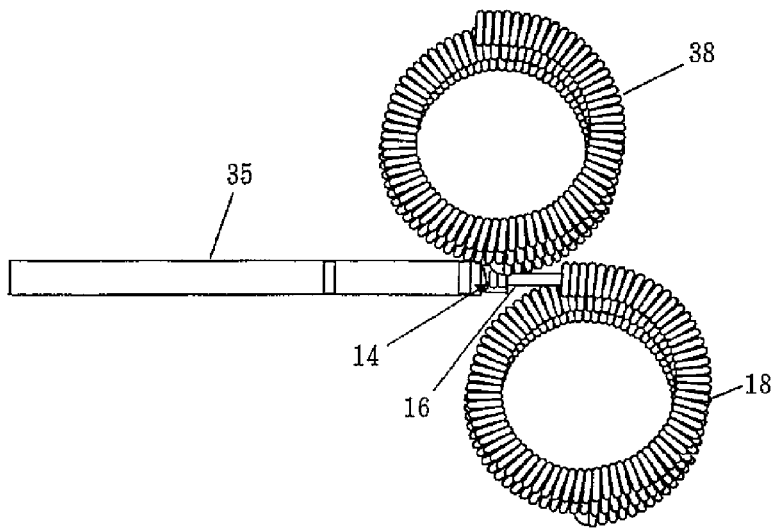
FIG. 8 is an explanatory view illustrating a state that a leaking member has been brought into contact in the test for releasing the intracorporeally indwelling member in FIG. 7.

As illustrated in FIG. 8, a leaking member 38 composed of another intracorporeally indwelling member having the same construction and form as the intracorporeally indwelling member 18 was further arranged in a state coming into contact with the leading end part 14 of the wire body 10. In this state, an output terminal 37 of the high-frequency power source device 36 was connected to the base end part 12 of the wire body 10 to supply a high-frequency current having a frequency of 300 kHz and electric power of 0.7 W, thereby performing a test for releasing the intracorporeally indwelling member.

As a result, the connecting member 16 in the medical wire was fused in a moment, and the intracorporeally indwelling member 18 was released.

From the above result, in the leading end part of the medical wire, the contact of a leaking member such as an intracorporeally indwelling member previously arranged with the exposed surface portions of the coil piece, which form the heating electrode portion, i.e., the electrode-forming portion is effectively inhibited by the non-conductive coating film even when the leaking member comes into contact with the leading end part of the wire body. As a result, the current is prevented from leaking into the leaking member. It is therefore apparent that the connecting member can be surely fused, and the intracorporeally indwelling member can be surely released.

Comparative Example 1

Figure 9:
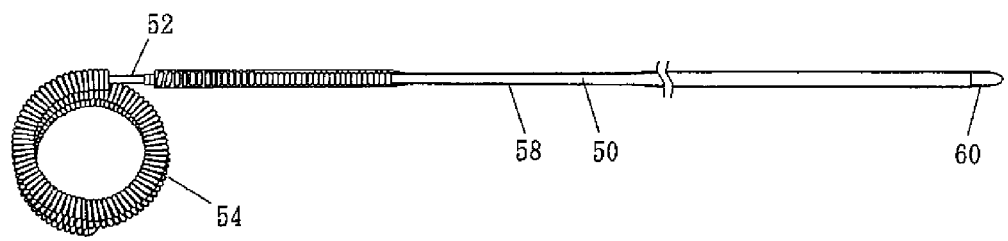
FIG. 9 is a side elevation illustrating the construction of an exemplary conventional medical wire.
Figure 10:
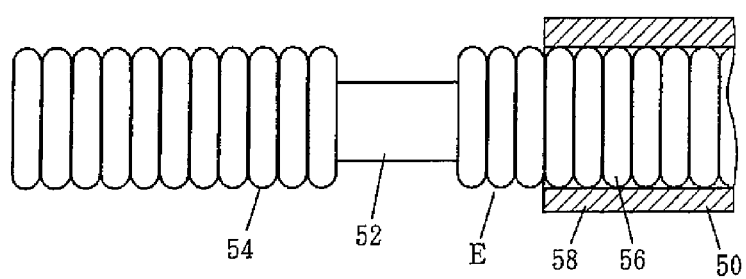
FIG. 10 is an explanatory side elevation illustrating, on an enlarged scale, a joint portion between a leading end part of a wire body and an intracorporeally indwelling member in the medical wire shown in FIG. 9.

A test for releasing an intracorporeally indwelling member was performed in the same manner as in Example 1 except that a medical wire of the construction shown in FIG. 9 and FIG. 10 was used for the medical wire. As a result, the connecting member 52 was not fused, and the intracorporeally indwelling member 54 was not released.

From the above result, it is understood that leak is caused, the connecting member cannot be fused, and the intracorporeally indwelling member cannot be released when the leaking member comes into contact with the leading end part of the wire body.

Although Example of the present invention has been described above, various kinds of intracorporeally indwelling members may be used as the intracorporeally indwelling member. Accordingly, the present invention can be applied in the whole treatment, in which other thrombus-forming members than coils, and other various intracorporeally indwelling members having a medical effect or medically auxiliary effect by their leaving are separated from the conductive wire body.

The invention claimed is:

1. A medical wire comprising:
a conductive wire body, and an intracorporeally indwelling member connected to a leading end part of the conductive wire body through a thermally-fusible connecting member, wherein the connecting member is adapted to be heated and fused by supplying an electric current for fusion through the conductive wire body, thereby releasing the intracorporeally indwelling member,
wherein a non-conductive coating film is formed on an external peripheral surface of an electrode-forming portion in the leading end part of the wire body, and a part of the surface of the wire body is exposed through the coating film, thereby forming a heating electrode portion,
wherein the heating electrode portion is formed by a plurality of fine cutout portions formed in the coating film,
wherein the intracorporeally indwelling member is formed by a coil material comprising a coiled metal filament, and a maximum width of the cutout portions is less than an outer diameter of the coil material forming the intracorporeally indwelling member,
wherein the cutout portions are adapted to assist fusing of the thermally-fusible connecting member, and
wherein the exposed part of the surface of the wire body is adapted to come into contact with body fluid.

2. The medical wire according to claim 1, wherein a total area of the plurality of the cutout portions is at least 0.01 mm$^2$.

3. The medical wire according to one of claims 1 and 2, wherein a thickness of the coating film is 0.001 to 0.1 mm.

4. The medical wire according to one of claims 1 and 2, wherein the cutout portions comprise at least one of circular openings and semicircular depressed cutouts formed from a leading edge of the coating film.

5. The medical wire according to one of claims 1 and 2, wherein at least one of the cutout portions is a depressed cutout formed from a leading edge of the coating film.

6. The medical wire according to one of claims 1 and 2, wherein the cutout portions comprise three semicircular depressed cutouts formed from a leading edge in the coating film, and three circular openings formed in a region located on a hand side from the leading edge.

7. The medical wire according to one of claims 1 and 2, wherein a material of the metal filament is selected from platinum, tungsten, gold, tantalum, iridium, palladium, and alloys thereof.

8. The medical wire according to one of claims 1 and 2, wherein a material of the coating film is selected from polytetrafluoroethylene, fluorinated ethylene-propylene resins, polyalkylene fluoride, polyethylene, polyethylene terephthalate, polyamide, and polyimide.

9. The medical wire according to one of claims 1 and 2, wherein the cutout portions comprise at least one of elliptical openings and semi-elliptical depressed cutouts formed from the leading edge of the coating film.

10. The medical wire according to claim 1, wherein the medical wire is adapted to be introduced into a body with the intracorporeally indwelling member in a lead position from a proximal operating part of a microcatheter.

11. The medical wire according to claim 1, wherein the cutout portions comprise a plurality of triangular depressed cutouts formed from a leading edge in the coating film, and a plurality of square openings formed in a region located on a hand side from the leading edge.

* * * * *